United States Patent
Fabio et al.

(10) Patent No.: US 11,013,691 B2
(45) Date of Patent: *May 25, 2021

(54) HEAT-STABLE DRY POWDER PHARMACEUTICAL COMPOSITIONS AND METHODS

(71) Applicant: MannKind Corporation, Westlake Village, CA (US)

(72) Inventors: Karine Fabio, Woodbury, CT (US); Joseph J. Guarneri, Stamford, CT (US); Kieran Curley, Cos Cob, CT (US); Marshall L. Grant, Newtown, CT (US); Andrea Leone-Bay, Ridgefield, CT (US)

(73) Assignee: MannKind Corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/529,040

(22) Filed: Aug. 1, 2019

(65) Prior Publication Data

US 2019/0358163 A1 Nov. 28, 2019

Related U.S. Application Data

(60) Division of application No. 15/885,416, filed on Jan. 31, 2018, now Pat. No. 10,413,513, which is a continuation of application No. 14/905,236, filed as application No. PCT/US2014/047304 on Jul. 18, 2014, now Pat. No. 9,925,144.

(60) Provisional application No. 61/847,981, filed on Jul. 18, 2013.

(51) Int. Cl.
| | | |
|---|---|---|
| A61K 38/12 | (2006.01) | |
| A61K 9/16 | (2006.01) | |
| A61K 38/095 | (2019.01) | |
| A61K 9/00 | (2006.01) | |
| A61K 38/23 | (2006.01) | |
| A61K 38/26 | (2006.01) | |
| A61K 38/28 | (2006.01) | |
| A61K 38/29 | (2006.01) | |
| A61K 45/06 | (2006.01) | |
| A61K 31/198 | (2006.01) | |
| A61K 31/4172 | (2006.01) | |

(52) U.S. Cl.
CPC .......... *A61K 9/1623* (2013.01); *A61K 9/0073* (2013.01); *A61K 9/1611* (2013.01); *A61K 9/1617* (2013.01); *A61K 31/198* (2013.01); *A61K 31/4172* (2013.01); *A61K 38/095* (2019.01); *A61K 38/12* (2013.01); *A61K 38/23* (2013.01); *A61K 38/26* (2013.01); *A61K 38/28* (2013.01); *A61K 38/29* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,794,357 B1* | 9/2004 | Backstrom | ........... | A61K 9/0075 424/489 |
| 6,835,372 B2* | 12/2004 | Kuo | ..................... | A61K 9/0075 424/9.34 |
| 6,998,137 B2* | 2/2006 | Shih | ........................ | A61K 9/143 424/426 |
| 8,372,804 B2* | 2/2013 | Richardson | .......... | A61K 9/0075 514/5.3 |
| 9,925,144 B2* | 3/2018 | Fabio | ................... | A61K 9/1617 |
| 10,159,644 B2* | 12/2018 | Smutney | ................ | A61K 39/12 |
| 10,413,513 B2* | 9/2019 | Fabio | ..................... | A61K 38/28 |
| 2009/0111749 A1* | 4/2009 | Richardson | ............... | A61P 5/00 514/1.1 |

OTHER PUBLICATIONS

Marconi, Journal of Food, Composition and Analysis 11, 178-187 (1998) (Year: 1998).*
Hawe, Pharmaceutical Research 26, 1679-1688 (2009) (Year: 2009).*

* cited by examiner

*Primary Examiner* — Satyanarayana R Gudibande
(74) *Attorney, Agent, or Firm* — K&L Gates LLP; Louis C. Cullman; Hal Gibson

(57) ABSTRACT

Disclosed herein are heat-stable dry powders which include peptides or protein such as oxytocin for use as a pharmaceutical composition. The composition is highly stable at increased temperatures and relatively high humid environments, and are intended for storage at room temperature with an improved shelf-life. In particular, the dry powders are intended for inhalation, however, other routes of administration can be used when reconstituted in solution.

11 Claims, 4 Drawing Sheets

HEAT-STABLE DRY POWDER PHARMACEUTICAL COMPOSITIONS AND METHODS

CROSS REFERENCE TO RELATED APPLICATIONS

This application is a divisional of U.S. patent application Ser. No. 15/885,416, filed Jan. 31, 2018, which is a continuation of U.S. patent application Ser. No. 14/905,236, filed Jan. 14, 2106, now U.S. Pat. No. 9,925,144, which is a 371 of PCT/US2014/047304, filed Jul. 18, 2014, which claims benefit under 35 U.S.C. § 119(e) from U.S. Provisional Patent Application Ser. No. 61/847,981, filed Jul. 18, 2013, the content of each of which is incorporated herein by reference in its entirety.

TECHNICAL FIELD

Disclosed herein are heat-stable dry powder compositions and methods for delivering biodegradable substances, including peptides and proteins, and systems and methods for delivering the dry powders. In particular, the dry powders are preferably intended for pulmonary delivery by inhalation to treat certain disorders and/or diseases, including post-partum hemorrhaging.

BACKGROUND

Delivery of drugs has been a major problem for many years, particularly when the compound to be delivered is unstable under the conditions encountered in the gastro-intestinal tract when administered orally to a subject, prior to reaching its targeted location. For example, it is preferable in many cases to administer drugs orally especially in terms of ease of administration, patient compliance, and decreased cost. However, many compounds are ineffective or exhibit low or variable potency when they are administered orally. Presumably this is because the drugs are unstable under conditions in the digestive tract or because they are inefficiently absorbed. For biologic products, in particular peptides and proteins, the acidic environment in the stomach is detrimental to maintain function as most proteins are degraded readily.

Isolated biological substances, including, certain proteins and peptides can readily and completely lose functional activity, for example, by taking them out of −20° C. storage once. Other isolated proteins and peptides undergo significant degradation when stored at 4° C., without the addition of protease inhibitors. Most mammalian proteins and peptides degrade at a temperature greater than 43° C. It has been well established that at 55° C., most proteins undergo complete denaturation in about 1-2 hours. In some cases, complete denaturation and destabilization of an isolated protein also occurs at room temperature.

Due to the problems associated with oral drug delivery of drugs and in particular, biologically-derived products, drug delivery to the lungs has been explored. For example, drugs delivered to the lungs are designed to have an effect on the tissue of the lungs, for example, vasodilators, surfactants, chemotherapeutic agents or vaccines for flu or other respiratory illnesses. Drug formulations for treating pulmonary diseases such as asthma are available by several methods, including, using nebulizers such as treatment with PULMOZYME®, using metered-dose inhalers such as SYMBICORT®, and dry powder inhalers such as ADVAIR DISKUS®, PULMICORT FLEXAHER®. Other drugs, including nucleotide drugs, have been delivered to the lungs because they represent a tissue particularly appropriate for treatment, for example, for genetic therapy in cystic fibrosis, where retroviral vectors expressing an effective adenosine deaminase are administered to the lungs.

Currently, formulations for treating systemic disease using biologic products are available primarily through injectable compositions. Dry powder compositions for pulmonary inhalation and systemic delivery of insulin have been used including EXUBERA®, and AFREZZA® in clinical trials. There is the desire, however, to improve the shelf-life at room temperature for dry powder compositions, especially those comprising a biologic molecule, including peptides and nucleic acids, to further prolonged their life, facilitate their storage and delivery prior to patient use, particularly if refrigeration is not available.

For example, according to the World Health Organization, 800 women die every day from pregnancy or childbirth-related complications. Among the major causes of death is severe bleeding (post-partum hemorrhage) that can be prevented by the use of a peptide hormone, oxytocin, a biologic molecule. Commercially available oxytocin compositions are provided as liquid formulations under the trade names PITOCIN® and SYNTOCINON® or as generic oxytocin; the peptide in solution degrades readily at ambient temperature, requires storage below 25° C. prior to use, and is administered only by injection. The preparations of injectable formulations and special storage needed create challenges, which prohibit their use in subtropical and tropical climates where there is a great need, and refrigeration and sterilization are not always readily available.

Accordingly, there is room for improvement in the development of pharmaceutical formulations comprising biologic molecules in particular for pulmonary delivery in the treatment of disease.

SUMMARY

The present disclosure provides dry powder compositions for inhalation which are stable at room temperature or higher temperatures for prolonged periods of time without substantially losing their biological activity. In one embodiment, a pharmaceutical formulation is provided comprising a dry powder for inhalation comprising a biologic molecule, wherein the biologic molecule comprises a peptide or a protein for systemic delivery using a dry powder inhalation system comprising an inhaler that can be used with a unit dose cartridge or capsule for multiple use, a single use inhaler with an integrally built-in container for single use, or a multidose inhaler provided with a plurality of doses integrally configured with the inhaler.

In one embodiment, a heat-stable pharmaceutical formulation is provided comprising, a dry powder comprising a protein or a peptide and one or more pharmaceutically acceptable carriers and/or excipients, which formulations are stable at high temperatures and high humidity. In one embodiment, the pharmaceutical formulation is stable for a long period of time at temperatures, for example, temperatures greater than 20° C., greater than 25° C., greater than 30° C., or greater than 35° C.; and relative humid environments such as environments having a relative humidity greater than 5%, greater than 10%, greater than 30%, greater than 50%, greater than 60%, or greater than 70%; wherein the pharmaceutically acceptable carriers and/or excipients include, for example, buffers, salts, polymers, diketopiperazines and/or salts thereof, and the like. In one embodiment, the dry powder compositions can optionally include surfactants such as polysorbates, for example, polysorbate 80 and Tween.

In a certain embodiments, the formulation comprises a dry powder comprising a peptide, including, for example, oxytocin, an oxytocin derivative or an analog thereof such as carbotecin; a buffer, and a monovalent or divalent cationic salt, and optionally a sugar and/or an amino acid. In a particular embodiment, the formulation comprises a dry powder comprising oxytocin, an oxytocin derivative, or an oxytocin analog; a buffer and/or a divalent cation or monovalent cation provided by a salt, including, zinc citrate, zinc acetate, disodium tartrate, mono-sodium tartrate, sodium citrate, disodium citrate, trisodium citrate, zinc chloride, calcium chloride, magnesium chloride, sodium hydroxide, and the like. In one embodiment, the formulation further comprises one or more amino acids, including leucine, isoleucine, trileucine, cystine, arginine, lysine, methionine, and/or histidine. In an embodiment, the monovalent cation in the formulation can include sodium, potassium and lithium. In an alternate embodiment, the formulation may be provided with citric acid.

In a specific embodiment, a dry powder composition is provided comprising oxytocin, sodium citrate, including, monovalent, divalent or trivalent form, in an amount less than 40% (w/w), less than 30% (w/w), less than 20% (w/w), or less than 10% (w/w), and zinc chloride or zinc citrate in an amount less than 35% (w/w), less than 20% (w/w), or less than 10% (w/w) in the composition. In a particular embodiment, the zinc chloride is used in an amount ranging from about 1% to about 7% (w/w) of the composition. In an alternative embodiment, the zinc citrate is used in an amount ranging from about 9% to about 35% (w/w) of the composition.

In a specific embodiment, a dry powder composition is provided comprising oxytocin, sodium tartrate, including, monovalent, or divalent form, in an amount less than 40% (w/w), less than 30% (w/w), less than 20% (w/w), or less than 10% (w/w), and zinc chloride or zinc citrate in an amount less than 35% (w/w), less than 20% (w/w), or less than 10% (w/w) in the composition. In a particular embodiment, the zinc chloride is used in an amount ranging from about 1% to about 7% (w/w) of the composition. In an alternative embodiment, the zinc tartrate is used in an amount ranging from about 9% to about 35% (w/w) of the composition.

In one embodiment, the dry powder composition comprises citrate salts in an amount ranging from 100 to 20 equivalents per mole of oxytocin, an oxytocin analog or derivative thereof; and the amount of zinc salts can range from 50 to 5 equivalents per mole of oxytocin in the composition. In some embodiments, concentrated sodium citrate buffers were used as the source of citrate; wherein the citrate buffers had a concentration up to 0.1 M or 0.75 M and range in pH values of 4.0 to 6.5.

In one embodiment, the dry powder composition comprises oxytocin or an analog or derivative thereof; zinc and citrate, wherein the oxytocin, analog or derivative thereof is in an amount up to 200 IU in a single inhalable dose. In some embodiments, the dry powder composition comprises 150 IU, 100 IU, 50 IU, 40 IU, 20 IU, 10 IU, 5 IU, 1 IU, 0.05 IU, or 0.005 IU of oxytocin, an analog or a derivative thereof in a single inhalable dose.

A method of making a dry powder formulation comprising mixing or homogenizing a solution comprising a peptide or protein or analog thereof, wherein the solution comprises citrate salts in an amount ranging from 100 to 20 equivalents per mole of the peptide or protein; and an amount of zinc salts can range from 50 to 5 equivalents per mole of the peptide or protein or analog thereof in the composition. In some embodiments, concentrated sodium citrate buffers were used as the source of citrate; and spray-drying a solution in a nitrogen gas chamber, comprising a peptide, protein, fragments thereof and/or analogs thereof, wherein the dry powder formulation comprises a mixture of the peptide, protein, fragments thereof and/or analogs thereof; a citrate or tartrate and a cationic salt at a pH ranging from pH 4.5 to pH 6.5, and wherein the cationic salt is a divalent cationic salt.

Embodiments include a method for treating post-partum hemorrhaging comprising administering to a subject in need of treatment a dry powder formulation by inhalation, the composition comprising oxytocin, an analog thereof or derivative thereof; a citrate or tartrate and a source of a cation, including, zinc within 24 hours post-partum. In one embodiment, the treatment comprises administrating one or more doses of the dry powder formulation described herewith immediately upon childbirth.

In an alternate embodiment, a method of preventing post-partum hemorrhage comprising administering to a subject susceptible of post-partum hemorrhage a dry powder formulation comprising oxytocin, an analog thereof or derivative thereof; a citrate or tartrate, and a source of a cation, including, zinc within 24 hours or immediately after childbirth.

In other embodiments described herewith, there are disclosed methods for making heat-stable and humidity-stable formulations and methods for using the formulations in the treatment of diseases and/or disorders including, for example, post-partum hemorrhaging, autism, social anxiety disorders; mood disorders, and other hormone-related diseases, in embodiments using an inhalation system. In an exemplary embodiment, the inhalation system is a high resistance inhaler for single dose usage.

BRIEF DESCRIPTION OF THE DRAWINGS

The following drawings form part of the present specification and are included to further demonstrate certain aspects of the examples disclosed herein. The disclosure may be better understood by reference to one or more of these drawings in combination with the detailed description of specific embodiments presented herein.

DETAILED DESCRIPTION

Figure 1A:
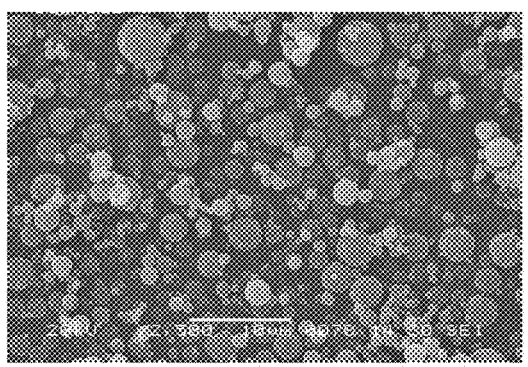
FIGS. 1A and 1B are scanning electron micrographs of an amorphous dry powder formulation embodiment comprising 1% oxytocin, 87% trehalose; 10% isoleucine and 10% polyvinylpirrolidone (PVP) at low (1A) and high magnification (1B).

Drug delivery to the lungs offers many advantages. It is difficult to deliver drugs into the lungs due to problems in transporting the drugs past natural physical barriers in a uniform volume and weight of the drug and the drug physical and chemical characteristics. Disclosed herein are heat-stable formulations comprising, a buffer, including, citrate, and a monovalent, or divalent cation, and one or more pharmaceutically acceptable carriers and/or excipients. Embodiments disclosed herein show that the dry powder formulations are stable at high heat and humidity and thus they facilitate and overcome the storage and refrigeration challenges posed by prior art formulations. A method of making the dry powder composition for extended storage at temperatures greater than 20° C. and humid environments if also provided.

As used herein, the term "microparticle" refers to a particle with a diameter of about 0.5 to about 1000 μm, irrespective of the precise exterior or interior structure. Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. To reach the deep lung (or alveolar region) where most efficient absorption is believed to occur, it is preferred to maximize the proportion of particles contained in the "respirable fraction" (RF), generally accepted to be those particles with an aerodynamic diameter of about 0.5 to about 6 microns, though some references use somewhat different ranges, as measured using standard techniques, for example, with an Anderson Cascade Impactor. Other impactors can be used to measure aerodynamic particle size such as the NEXT GENERATION IMPACTOR™ (NGI™, MSP Corporation), for which the respirable fraction is defined by similar aerodynamic size, for example <6.4 μm. In some embodiments, a laser diffraction apparatus is used to determine particle size, for example, the laser diffraction apparatus disclosed in U.S. patent application Ser. No. 12/727, 179, filed on Mar. 18, 2010, which is incorporated herein in its entirety for its relevant teachings related to laser diffraction, wherein the volumetric median geometric diameter (VMGD) of the particles is measured to assess performance of the inhalation system. For example, in various embodiments cartridge emptying of ≥80%, 85%, or 90% and a VMGD of the emitted particles of ≥12.5 μm, ≥7.0 μm, or ≥4.8 μm can indicate progressively better aerodynamic performance.

As used herein, the term "about" is used to indicate that a value includes the standard deviation of the measurement for the device or method being employed to determine the value.

Respirable fraction on fill (RF/fill) represents the % of powder in a dose that is emitted from an inhaler upon discharge of the powder content filled for use as the dose, and that is suitable for respiration, i.e., the percent of particles from the filled dose that are emitted with sizes suitable for pulmonary delivery, which is a measure of microparticle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes <5.8 μm as measured using standard techniques.

As used herein, the term "dry powder" refers to a fine particulate composition that is not suspended or dissolved in a propellant, or other liquid. It is not meant to necessarily imply a complete absence of all water molecules.

As used herein, "amorphous powder" refers to dry powders lacking a definite repeating form, shape, or structure, including all non-crystalline powders.

In one embodiment, the dry powder is a relatively cohesive powder which requires optimal deagglomeration condition. In one embodiment, the inhalation system provides a re-useable, miniature breath-powered inhaler in combination with single-use cartridges containing pre-metered doses of a dry powder formulation.

As used herein the term "a unit dose inhaler" refers to an inhaler that is adapted to receive or comprises a single container comprising a dry powder formulation and delivers a single dose of a dry powder formulation by inhalation from the container to a user. In some instances multiple unit doses will be required to provide a user with a specified dosage. In one embodiment, the inhaler is a dry powder inhaler, which can be disposable for single use, or reusable for multiple uses with a single unit dose container.

As used herein the term "a multiple dose inhaler" refers to an inhaler having a plurality of containers, each container comprising a pre-metered dose of a dry powder medicament and the inhaler delivers a single dose of a medicament powder by inhalation at any one time.

As used herein a "container" is an enclosure configured to hold or contain a dry powder formulation, a powder containing enclosure, and can be a structure with or without a lid. This container can be provided separately from the inhaler or can be structurally integrated within the inhaler (e.g. non-removable). Further, the container can be filled with a dry powder. A cartridge can also include a container.

As used herein a "powder mass" refers to an agglomeration of powder particles or agglomerate having irregular geometries such as width, diameter, and length.

As used herein, the term "microparticle" refers to a particle with a diameter of about 0.5 to about 1000 μm, irrespective of the precise exterior or interior structure. However four pulmonary delivery microparticles that are less than 10 μm are generally desired, especially those with mean particles sizes of less than about 5.8 μm in diameter.

In an exemplary embodiment, a dry powder formulation is provided, comprising, a peptide or a protein, wherein the peptide or protein is sensitive to degradation by heat. In a particular embodiment, the dry powder formulation comprises a peptide including, oxytocin, an oxytocin derivative, or an oxytocin analog; a citrate, including; sodium citrate and zinc citrate; a divalent salt; including zinc chloride; calcium chloride and magnesium chloride; and one or more pharmaceutically acceptable carriers selected from sugars, for example, saccharides, disaccharides; oligosaccharides; an amino acid; wherein the sugar is, for example, trehalose, mannose, mannitol or sorbitol, and the carrier is polyethylene glycol, polyvinylpyrrolidone, or a diketopiperazine capable of forming microparticles, including, fumaryl diketopiperazine, succinyl diketopiperazine, maleyl diketopiperazine, malonyl diketopiperazine and oxalyl diketopiperazine, or the disodium or magnesium salt thereof, and derivatives thereof.

In another embodiment, the formulation comprises a peptide, including, growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, enkephalin, adrenocorticotropic hormone, growth hormone-releasing hormone, growth factors, including, granulocyte colony formation-stimulating factor; thyroid stimulating hormone, thyroid-stimulating hormone-releasing hormone, antinociceptive peptides, angiotensin, prolactin, luteinizing hormone, rennin, gastric inhibitory polypeptide (GIP), and C-peptide.

In another embodiment, the formulation comprises a peptide, wherein the peptide is oxytocin, insulin, growth hormone, calcitonin, glucagon, parathyroid hormone, glucagon-like peptide-1, glucagon like-peptide-2, parathyroid hormone (1-34), or parathyroid hormone releasing hormone, oxyntomodulin, peptide YY, leptin, deoxyribonuclease, ribonuclease, and follicle stimulating hormone.

In one embodiment, the formulation comprises one or more peptides, one or more amino acid, wherein the amino acid is isoleucine, leucine, trileucine, cystine, cysteine, glycine, lysine, arginine, histidine, or methionine; and one or more sugars, including, lactose, mannitol, mannose, sorbitol, trehalose, and the like. In this and other embodiments, the carrier can be polyethylene glycol, polyvinylpyrrolidone, or a saccharide, an oligosaccharide, or a polysaccharides, including lactose, trehalose, mannose, mannitol, or sorbitol; zinc citrate and zinc chloride; wherein the formulation is made by a spray-drying process wherein the peptide is in a buffered solution having a pH ranging from about pH 3.5 to about pH 7; or pH 4.5 to pH 6.5.

In a particular embodiment, the formulation comprises oxytocin in concentration from about 0.005 IU to about 40 IU, from 1 IU to about 15 IU; or from about 5 IU to about 20 IU. In one embodiment, oxytocin is administered to a patient to prevent post-partum hemorrhaging a few minutes after giving birth in a formulation comprising oxytocin in an amount ranging from 5 to about 40 IU in a single inhalation. In this embodiment, the content of oxytocin that can be provided in the formulation ranges from about 0.1% (w/w) to about 50% (w/w), from about 0.5% (w/w) to about 40% (w/w); from about 0.5% (w/w) to about 20% (w/w); or from about 1% (w/w) to about 10% (w/w). In certain embodiments, the amount of oxytocin can be greater than 40 IU depending in the need of the subject to be treated.

In one embodiment, there is provided a method for the effective delivery of a formulation to the blood stream of a subject, comprising providing to a subject in need of treatment an inhalation system comprising an inhaler including a cartridge containing a formulation comprising a dry powder formulation comprising a peptide including, oxytocin, a citrate buffer or tartrate buffer and a divalent cation salt, wherein the divalent cation is zinc. In this and other embodiments, the inhalation system delivers a powder plume comprising particles having a volumetric median geometric diameter (VMGD) less than 8 µm. In an example embodiment, the VMGD of the microparticles can range from about 4 µm to 6 µm. In an example embodiment, the VMGD of the powder particles can be from 3 µm to about 6 µm in a single inhalation of the formulation of fill mass ranging between 1 mg and 10 mg of dry powder. In this and other embodiments, the inhalation system delivers greater than 40%; or greater than 60% of the dry powder formulation from the cartridge.

In a further embodiment, the formulation is an amorphous dry powder comprising microparticles of disodium fumaryl diketopiperazine comprising oxytocin, a citrate buffer; zinc chloride, an amino acid, such as leucine, isoleucine, trileucine or cystine and mannitol or trehalose, or a combination thereof.

In an embodiment, the formulation comprises an amorphous dry powder comprising a peptide, including, a heat-sensitive peptide, including oxytocin; wherein the dry powder is formed by mixing oxytocin in a solution containing a citrate or acetate buffer at an adjusted pH ranging from 4.5 to 6.5 and adding a divalent cationic salt, including zinc chloride and optionally a sugar such as trehalose or mannitol prior to drying.

In a particular embodiment, the formulation comprises an amorphous dry powder comprising oxytocin; wherein the dry powder is formed by mixing oxytocin in a solution containing citrate salts and/or citric acid and adding a divalent cationic salt, including, zinc chloride and optionally a sugar such as trehalose or mannitol and optionally, one or more carriers.

Further embodiments concern drug delivery systems comprising an inhaler, a unit dose dry powder medicament container, and a dry powder comprising a heat-sensitive peptide as disclosed herein and zinc citrate.

One embodiment discloses a formulation comprising oxytocin, a derivative thereof, or an analog thereof, wherein the formulation further comprises diketopiperazine microparticles, including, microparticles of fumaryl diketopiperazine having a specific surface area (SSA) of less than about 67 $m^2/g$. Another embodiment includes diketopiperazine microparticles in which the specific surface area is from about 35 to about 67 $m^2/g$, within a 95% confidence limit. Another embodiment includes diketopiperazine microparticles in which the specific surface area is from about 35 to about 62 $m^2/g$. Another embodiment includes diketopiperazine microparticles in which the specific surface area is from about 40 to about 62 $m^2/g$.

In alternative embodiments, the FDKP microparticles comprise a drug or active agent. In various embodiments of the FDKP microparticles, the drug can be, for example, a peptide, including, oxytocin, insulin, glucagon-like peptide-1 (GLP-1), glucagon, exendin, parathyroid hormone, calcitonin, oxyntomodulin, derivatives and/or analogs thereof, and the like. In another embodiment of the FDKP microparticles, the peptide content can vary depending on downstream processing conditions. In a particular example, the FDKP microparticles can be prepared to have a drug/peptide content that can vary depending on the dose to be targeted or delivered. For example, wherein the drug is insulin, the insulin component can be from about 3 U/mg to about 6 U/mg in the powder formulation comprising the microparticles and the zinc salt and citrate can be added to solution prior to forming the particles. In certain embodiments, the drug is adsorbed to the surfaces of pre-formed microparticles.

Further embodiments concern drug delivery systems comprising a combination of an inhaler, a unit dose dry powder medicament container, for example, a cartridge, and comprising the dry powder formulations disclosed herein and an active agent. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 ($\sqrt{kPa}$)/liter per minute. In certain embodiments, the dry powders can be delivered effectively by inhalation with an inhalation system wherein the peak inhalation pressure differential can range from about 2 to about 20 kPa, which can produce resultant peak flow rates of about between 7 and 70 liters per minute. In certain embodiments, the inhalation system are configured to provide a single dose by discharging powder from the inhaler as a continuous flow, or as one or more pulses of powder delivered to a patient. In some embodiments disclosed herewith, the dry powder inhaler system comprises a predetermined mass flow balance within the inhaler. For example, a flow balance of approximately 10% to 70% of the total flow exiting the inhaler and into the patient is delivered by one or more dispensing ports, which airflow passes through the area containing the powder formulation, and wherein approximately 30% to 90% air flow is generated from other conduits of the inhaler. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 mg and 50 mg; or 1 mg to 30 mg. In certain embodiments, an inhalation system as described above can emit a respirable fraction/fill of a powder dose at percentages greater than 40% in a single inhalation, greater than 50%, greater than 60%, or greater than 70%.

In particular embodiments, an inhalation system is provided comprising a dry powder inhaler, and a dry powder formulation. In some aspects of this embodiment of the inhalation system, the dry powder formulation is provided in a unit dose cartridge. Alternatively, the dry powder formulation can be preloaded in the inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 µm. The inhalers can discharge greater than 85% of a powder medicament contained within a container during dosing. In certain embodiments, the inhalers can discharge greater than 85% of a powder medicament contained in a single inhalation. In one embodiment, the inhalers can discharge greater that 90% of the cartridge contents or container contents in less than 3 seconds at pressure differentials between 2 and 5 kPa with fill masses ranging up to 30 mg.

Another embodiment disclosed herein includes a method of making microparticles suitable for pulmonary administration as a dry powder formulation comprising, a carrier particle, including, diketopiperazine microparticles. In this and other embodiments, the dry powder formulation is obtained by spray-drying a solution containing a peptide, wherein the one or more excipients is dissolved in an aqueous solution comprising the zinc salt and citrate and mixed, followed by adding the amount of the peptide with mixing to form a feed solution; atomizing the flow of solution into a drying nitrogen gas flow at an inlet temperature of about 120° C. to 150° C. and an outlet temperature of about 60° C. to 65° C., or 50° C. to 75° C., or 40° C. to 85° C., or the like.

In some embodiments, the method of making diketopiperazine microparticles having the specific surface area of less than about 67 m²/g, and/or a trans isomer ratio of about 45% to 65%, which utilizes a diketopiperazine having the formula 3,6-bis(N—X-4-aminobutyl)-2,5-diketopiperazine disodium salt or magnesium salt, wherein X is selected from the group consisting of fumaryl, succinyl, maleyl, and glutaryl. In an exemplary embodiment, the diketopiperazine has the formula (bis-3,6-bis(N-fumaryl-4-aminobutyl)-2,5-diketopiperazine or 3,6-bis(N-fumaryl-4-amino-butyl)-2,5-diketopiperazine.

Another embodiment disclosed herein includes a method of delivering a drug, for example, a peptide such as insulin to a patient in need thereof comprising administering a dry powder to the deep lung by inhalation of the dry powder by the patient; wherein the dry powder comprises diketopiperazine microparticles comprising insulin, a zinc salt and citrate; wherein the microparticles are formed of a diketopiperazine and have a SSA ranging from about 35 to about 67 m²/g or about 40 to about 67 m²/g and/or in microparticles having a trans isomer content raging from about 45% to about 65%. In aspects of this embodiment, particular features of an inhaler system are specified. Further embodiments involve methods of treating an insulin-related disorder comprising administering a dry powder described above to a person in need thereof. In various embodiments an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder.

One embodiment comprises a method of treating an endocrine-related disease or disorder comprising administering to a person in need thereof a dry powder formulation comprising a peptide hormone, including, oxytocin, GLP-1 and the like, citrate and a divalent cationic salt. In one embodiment, the dry powder formulation can comprise disodium FDKP microparticles or FDKP microparticles having a specific surface area of less than about 67 m²/g and a drug suitable to treat said disease or disorder. Further embodiments include a method of treating an insulin-related disorder comprising administering a dry powder comprising microparticles of disodium FDKP or FDKP, a citrate, acetate or tartrate buffer and a divalent cation, including zinc, magnesium and calcium or a monovalent cation, including, sodium, potassium and lithium described above to a person in need thereof. The method can comprise administering to a subject a dry powder formulation. In various embodiments, a hormone-related disorder such as post-partum hemorrhage, or any other oxytocin-related disease can be treated with the formulation comprising oxytocin. In embodiments wherein an insulin-related disorder is to be treated, the formulation comprising insulin the subject to be treated can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises glucagon, an exendin, or GLP-1, PTH, PTHrP, combinations thereof, and the like.

In embodiments herewith, specific RF/fill values can depend on the inhaler used to deliver the powder. Powders generally tend to agglomerate and crystalline DKP microparticles form particularly cohesive powders. One of the functions of a dry powder inhaler is to deagglomerate the powder so that the resultant particles comprise a respirable fraction suitable for delivering a dose by inhalation. However, deagglomeration of cohesive powders is typically incomplete so that the particle size distribution seen when measuring the respirable fraction as delivered by an inhaler will not match the size distribution of the primary particles, that is, the profile will be shifted toward larger particles. Inhaler designs vary in their efficiency of deagglomeration and thus the absolute value of RF/fill observed using different designs will also vary. However, optimal RF/fill as a function of specific surface area will be similar from inhaler to inhaler.

One class of drug delivery agents that has been used to overcome problems in the pharmaceutical arts such as drug instability and/or poor absorption are the 2,5-diketopiperazines. 2,5-Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders these microparticles can be delivered by inhalation to specific areas of the respiratory system, including the lungs.

Such microparticles are typically obtained by pH-based precipitation of the free acid (or base) resulting in self-assembled microparticles comprised of aggregated crystalline plates. The stability of the particle can be enhanced by small amounts of a surfactant, such as polysorbate-80, in the DKP solution from which the particles are precipitated (see for example US Patent Publication No. 2007/0059373 entitled "Method of drug formulation based on increasing the affinity of crystalline microparticle surfaces for active agents" which is incorporated herein by reference in its entirety for all that it teaches regarding the formation and loading of DKP microparticles and dry powders thereof). Ultimately solvent can be removed to obtain a dry powder. Appropriate methods of solvent removal include lyophilization and spray drying (see for example US Patent Publication No. 2007/0196503 entitled "A method for improving the pharmaceutic properties of microparticles comprising diketopiperazine and an active agent" and U.S. Pat. No. 6,444,226 entitled "Purification and stabilization of peptide and protein pharmaceutical agents" each of which is incorporated herein by reference in its entirety for all that it teaches regarding the formation and loading of DKP microparticles and dry powders thereof). The microparticles disclosed herein can be composed of DKP free acid or bases or composed of DKP salts. Such particles are typically formed (as opposed to dried) by spray drying, resulting in spheres and/or collapsed spheres of an amorphous salt (as opposed to a free acid or base) so that they are chemically, physically, and morphologically distinct entities. In embodiments the present disclosure refers to FDKP as the free acid or the dissolved anion. In embodiments herewith, an exemplary embodiment includes the disodium salt of FDKP or FDKP disodium salt as disclosed and contemplated in U.S. Pat. Nos. 7,820,676 and 8,278,308, which are incorporated herein by reference in its entirety.

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference for all they disclose relating to diketopiperazine synthesis. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBzprotecting groups can be removed using 4.3 M HBr in acetic acid. This route can be preferred because it uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709,639, entitled, "Catalysis of Diketopiperazine Synthesis," which is also incorporated by reference herein for its teachings regarding the same.

Fumaryl diketopiperazine (3,6-bis(N-fumaryl-4-aminobutyl)-2,5-diketopiperazine; FDKP) is one preferred diketopiperazine for pulmonary applications:

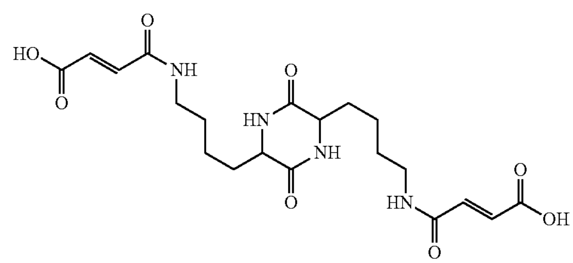 [SMILES: O=C(O)/C=C/C(=O)NCCCCC1NC(=O)C(CCCCNC(=O)/C=C/C(=O)O)NC1=O]

FDKP provides a beneficial microparticle matrix because it has low solubility in acid but is readily soluble at neutral or basic pH. These properties allow FDKP to crystallize and the crystals to self-assemble into form microparticles under acidic conditions. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP.

As noted, microparticles having a diameter of between about 0.5 and about 10 microns can reach the lungs, successfully passing most of the natural barriers. Particles in this size range can be readily prepared from diketopiperazines with acidic groups, such as the carboxylate groups in FDKP (as well as in related molecules such as 2,5-diketo-3,6-di(4-X-aminobutyl)piperazine wherein X is succinyl, glutaryl, or maleyl). Upon acid precipitation self-assembled particles composed of aggregates of crystalline plates are obtained. The size of these plates relates to the specific surface area of the particles which in turn is implicated in effects on the structure, loading capacity, and aerodynamic performance of the particles.

The SSA of DKP microparticles is a measure of average crystal size and can be used to gauge the relative contributions of crystal nucleation and growth to microparticle characteristics. SSA depends on the size of microparticle crystals and the density (ρ) of the microparticle matrix and is inversely proportional to the characteristic size, L, of the crystals. Embodiments disclosed herein show that microparticles with a specific surface area less than about 67 $m^2/g$ exhibit characteristics beneficial to delivery of drugs to the lungs such as improved aerodynamic performance with moderately efficient inhalers such as the MEDTONE® inhaler disclosed in U.S. Pat. No. 7,464,706 entitled, "Unit Dose Cartridge and Dry Powder Inhaler," which is incorporated by reference herein for its teachings regarding the same. An alternate embodiment with a specific surface area less than about 62 $m^2/g$ provides a greater level of assurance that a batch of particles will meet a minimum aerodynamic performance standard. As SSA also affects drug loading/ content capacity, various embodiments require SSA 40, or 45 m²/g for improved drug adsorption capacity. Additionally, as SSA falls below about 35 m²/g inconsistent cartridge emptying is observed even with high efficiency inhalers such as those disclosed in U.S. patent application Ser. No. 12/484,125 (now U.S. Pat. No. 8,499,757, entitled, "A Dry Powder Inhaler and System for Drug Delivery," filed on Jun. 12, 2009, and U.S. patent application Ser. No. 12/717,884, now U.S. Pat. No. 8,485,180, entitled, "Improved Dry Powder Drug Delivery System," filed on Mar. 4, 2010, which disclosures are herein incorporated by reference for its teachings regarding the same.

FDKP Microparticle Formation.

The first step in the manufacture of FDKP microparticles is the formation of the microparticles by pH-induced crystallization of FDKP and the self-assembly of the FDKP crystals into microparticles having an overall spherical morphology (FIG. 2). Accordingly, the manufacture of microparticles is essentially a crystallization process. Excess solvent can be removed by washing the suspension by repeated centrifugation, decantation and re-suspension, or by diafiltration.

In one embodiment, to form peptide-loaded FDKP microparticles, for example, insulin can be adsorbed directly onto the microparticles while in suspension (i.e. prior to freeze drying) by adding an insulin stock solution to the FDKP microparticle suspension comprising a citrate buffer. In embodiments, a pH control step can also be performed after the addition of the insulin stock solution. This step can promote insulin adsorption onto the microparticles in suspension prior to further processing. Increasing the pH of the suspension to about 4.5 promotes complete insulin adsorption onto the microparticles in suspension without excessive dissolution of the FDKP from the particle matrix and also improves the stability of insulin in the bulk drug product. The suspension can be flash-frozen drop-wise (i.e. cryopelletized) in liquid nitrogen and lyophilized to remove the solvent and obtain a dry powder. In alternative embodiments the suspension can be spray-dried to obtain the dry powder.

In one embodiment, a manufacturing process for making the present FDKP microparticles containing insulin is provided. In summary, using a high shear mixer such as a Dual-feed SONOLATOR™ at 2000 psi through a 0.001-in² orifice, or for example, the high shear mixer as disclosed in U.S. Provisional Patent Application Ser. No. 61/257,311, filed on Nov. 2, 2009, which disclosure is incorporated herein by reference in its entirety for all that it teaches regarding the production of DKP microparticlesparticles, equal masses of about 10.5 wt % acetic acid and about 2.5 wt % FDKP solutions at about 16° C.±about 2° C. can be fed at 2000 psi through a 0.001-in² orifice. The precipitate can be collected in a deionized (DI) water reservoir of about equal mass and temperature. The resultant suspension comprises about 0.8% solids. The precipitate can be concentrated and washed by tangential flow filtration. The precipitate can be first concentrated to about 4% solids then washed with deionized water. The suspension can be finally concentrated to about 10% solids based on the initial mass of FDKP. The concentrated suspension can be assayed for solids content by an oven drying method. In this embodiment, the FDKP microparticles in suspension are homogenized with zinc and citrate solution containing the insulin to form the powder particles then sprayed dried or lyophilized.

The microparticles described herein can comprise one or more active agents. As used herein "active agent", used interchangeably with "drug", refers to pharmaceutical substances, including small molecule pharmaceuticals, biologicals and bioactive agents. Active agents can be naturally occurring, recombinant or of synthetic origin, including proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), F(ab)$_2$, a single-chain antibody alone or fused to other polypeptides or therapeutic or diagnostic monoclonal antibodies to cancer antigens. The active agents can fall under a variety of biological activity and classes, such as vasoactive agents, neuroactive agents, hormones, anticoagulants, immunomodulating agents, cytotoxic agents, antibiotics, antiviral agents, antigens, infectious agents, inflammatory mediators, hormones, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-12, LTB receptor blockers including LY29311, BIIL 284 and CP105696, triptans such as sumatriptan and palmitoleate, insulin and analogs thereof, growth hormone and analogs thereof, parathyroid hormone (PTH) and analogs thereof, parathyroid hormone related peptide (PTHrP), ghrelin, obestatin, enterostatin, granulocyte macrophage colony stimulating factor (GM-CSF), amylin, amylin analogs, glucagon-like peptide 1 (GLP-1), Texas Red, clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide.

The drug content to be delivered depends on the need of the subject and the potency of the drug. In certain embodiments, microparticles formed from FDKP having a trans isomer content between 45% and 65% is typically greater than 0.01% are used. In one embodiment, the drug content to be delivered with the microparticles having the aforementioned trans isomer content, can range from about 0.01% to about 20%, which is typical for peptides such as insulin. For example, if the drug is insulin, the present microparticles typically comprise 3-6 U/mg (approximately 10 to 15%) insulin. In certain embodiments, the drug content of the particles can vary depending on the form and size of the drug to be delivered.

The range of loading of the drug to be delivered is typically between about 0.01% and about 90%, depending on the form and size of the drug to be delivered and the potency of the dose required. For oxytocin, preferred loads are about 0.5% to about 50% (w/w); or from about 0.5% (w/w) to about 20% (w/w).

As long as the DKP microparticles described herein retain the required isomer content, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. patent application Ser. No. 11/532,063, now U.S. Pat. No. 7,799,344, entitled "Method of Drug Formulation based on Increasing the Affinity of Crystalline Microparticle Surfaces for Active Agents" which is incorporated by reference herein for its teachings regarding the same. U.S. patent application Ser. No. 11/532,065, entitled "Method of Drug Formation based on Increasing the Affinity of Active Agents for Crystalline Microparticle Surfaces" describes methods for promoting adsorption of active agents onto microparticles. U.S. patent application Ser. No. 11/532,065, now U.S. Pat. No. 7,803,404 is also incorporated by reference herein for its teachings regarding the same.

EXAMPLES

The following examples are included to demonstrate embodiments of the disclosed microparticles. It should be appreciated by those of skill in the art that the techniques disclosed in the examples which follow represent techniques discovered by the inventor to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result.

Example 1

Preparation, Characterization and Stability of Oxytocin Spray-Dried Powders

Fourteen powders containing 1% (w/w) oxytocin and varying amounts of buffers, salts, carriers, excipients, including, trehalose, PVP, isoleucine, cystine, trileucine, FDKP, sodium citrate and zinc salt, obtained from various vendors as described in Table 1 below, were prepared at the 7 g scale as shown on Table 2 below. The samples were prepared by weighing the amounts required as stated in Table 2 and dissolved in deionized water to form a solution or suspension, the oxytocin was added and mixed prior to spray drying. In the samples using the citrate buffer and the divalent cation, oxytocin was dissolved in the citrate buffer prior to adding the rest of the ingredients in the mixture. The solution or suspension was then spray-dried using the parameters as described in Table 3 below. Suspensions were homogenized in a high shear mixer prior to spray drying. The solutions were filtered through a 0.2 μm membrane prior to spray-drying.

The dry powders were collected and used in the experiments described below. Experiments were conducted to characterize the powders obtained using various techniques, including to measure the oxytocin content of various samples before and after incubation to determine yields, loss on drying (LOD), aerodynamic performance, particle size and particle morphology were evaluated. Stability studies were carried out using aliquots from each of the dry powder samples prepared, which had been incubated at 40° C. in a relative humidity of 75% (40° C./75% RH) in scintillation vials sealed with a fluoropolymer resin lined screw cap which had been placed in heat-sealed aluminum pouches for the time periods studied. Samples of the incubated material were taken at various times after onset of the experiments and up to approximately 7 months. The samples were evaluated by high performance liquid chromatography (HPLC) assay (see preparation described below) to determine the presence of the oxytocin in the samples and the degradation products. Oxytocin stability studies were performed up to 11 months for certain powders, including, Sample ID Nos. 4, 6 and 13 in Table 2.

TABLE 1

Formulation Components

| Chemicals | Supplier |
| --- | --- |
| FDKP Na | MannKind |
| PVP K30 | Spectrum |
| Trehalose | Alfa Aesar |
| L-isoleucine | Alfa Aesar |
| Trileucine | Bachem |
| Cystine | Alfa Aesar |
| Citric acid anhydrous | EMD |
| Trisodium citrate dihydrate | Alfa Aesar |
| Zinc chloride | Sigma Aldrich |
| Zinc citrate | Sigma Aldrich |
| Oxytocin | American peptide |

Büchi mini spray dryer B 290

Filtration unit fast PES membrane (0.2 μm) 150 mL system (Nalgene)

Homogenizer (Tekmar Tissumizer)

TABLE 2

Sample Formulations Contents

| Sample ID No. | Wt. % Target (dry basis) | | | | | |
| --- | --- | --- | --- | --- | --- | --- |
| | Citrate | $ZnCl_2$ | Trehalose | $Na_2$FDKP | ILE* | PVP |
| 1 | — | — | 87.00 | — | 10.00 | 2.00 |
| 2 | 24.03 | 6.76 | 59.94 | — | 6.89 | 1.38 |
| 3 | 12.01 | 3.38 | 73.47 | — | 8.45 | 1.69 |
| 4 | 4.81 | 1.35 | 81.59 | — | 9.38 | 1.88 |
| 5 | 24.03 | — | 65.89 | — | 7.57 | 1.51 |
| 6 | 27.73 | 6.76 | 56.69 | — | 6.52 | 1.30 |
| 7 | 27.73 | 6.76 | 38.44 | 19.55 | 6.52 | — |
| 8 | — | — | 59.00 | 30.00 | 10.00 | — |
| 9 | — | — | 44.00 | 44.00 | 10.00 | 1.00 |
| 10 | — | — | 89.00 | — | 10.00 | — |
| 11 | — | — | 87.00 | — | TLE* 10.00 | 2.00 |
| 12 | — | — | 87.00 | — | CYS* 10.00 | 2.00 |
| 13 | 24.03 | Zn citrate 30.30 | 39.26 | — | ILE 4.51 | 0.90 |

*ILE: isoleucine, TLE: trileucine, CYS: cystine.

Spray-dried powders were prepared with a target oxytocin content of 1%. Formulation contents are detailed in Table 2. A mixture having a ratio of 87:10:2 by weight of trehalose, isoleucine and PVP served as a matrix for control formulations of Samples ID Nos. 1 to 6. To this mixture were added sodium citrate and zinc. The quantities of citrate salts were varied from 100 to 20 equivalents per mole of oxytocin (24 to 4.8% of total weight). The quantities of the zinc salts were varied from 50 to 10 equivalents per mole of oxytocin (6.7 to 1.3% of total weight). Concentrated sodium citrate buffers (75 mM pH 4.5 and 6.5) were used as the source of citrate.

The solids content of the feed solutions was kept constant at 5%. Feed solutions were filtered prior spray-drying. One formulation containing FDKP appeared cloudy and was not filtered (Sample ID No. 7); mixtures containing trileucine, cystine and zinc citrate (Samples ID No. 11, 12 and 13) required homogenization and the resulting suspensions were kept under constant stirring during the spray-drying process. A suspension containing zinc citrate and citrate buffer was prepared as feed solution and homogenized in a high sheer mixing (Tissumizer homogenizer). A second solution containing oxytocin and the remaining excipients in water were added to the suspension and the final weight was adjusted to 140 g with deionized water.

TABLE 3

Spray-drying conditions

| | |
|---|---|
| Inlet: | 130° C. |
| Outlet: | 63° C. |
| Drying gas flow: | 60 mbar (nitrogen) |
| Atomization flow: | ~59.9 g/h |
| Aspirator | 80% |
| Pump | 5% |

Figure 3:
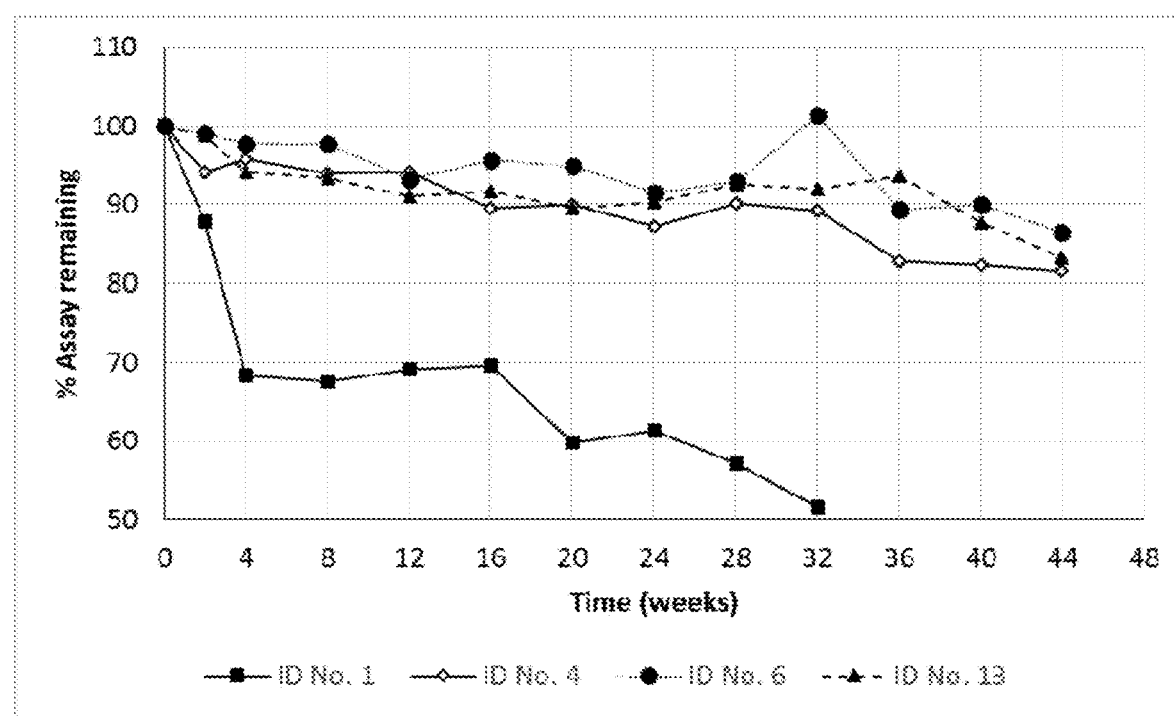
FIG. 3 provides a graphic representation of data obtained from stability studies data for dry powder composition embodiments comprising 1% oxytocin incubated at 40° C. and 75% relative humidity for a period of approximately 11 months compared to a control.

The oxytocin stability study results from are shown in Table 4 below. The data is shown as the percent (%) of oxytocin remaining in the sample compared to the starting amount of material used. As seen in Table 4 and FIG. 3, three of the powder formulations (Sample ID Nos. 4, 6, and 13) tested maintained more than about 90% of the oxytocin as assayed after 32 weeks of incubation. The data also show that the combination of sodium citrate and zinc salt led to the highest stability (less degradation of oxytocin) in solid or dry powder form (about 100%, Sample ID No. 6). Moreover, the addition of sodium citrate and zinc also led to higher respirable fraction per fill content of powder (RF/fill) used, with a maximum RF/fill of 60.2% for a powder containing 12% (w/w) sodium citrate, 3.4% (w/w) zinc chloride, 73.5% (w/w) trehalose, 8.4% (w/w) isoleucine and 1.69% (w/w) PVP. The control powder formulated without zinc and citrate, had a RF/fill of 40.9% (Sample ID No. 1), but its oxytocin degradation rate was more rapid as there was only 51.6% oxytocin remaining in the sample after 32 weeks of incubation.

Figure 1B:
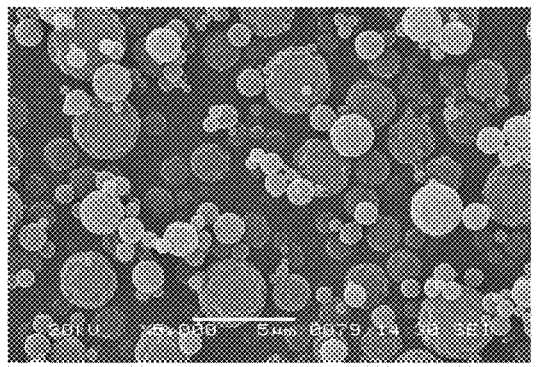

Scanning electron micrographs (SEM) of sample control powders were studied and shown in FIG. 1A (low magnification) and FIG. 1B. (high magnification The SEMs show regularly-shaped, substantially spherical particles, which appear substantially homogeneous in size with small surface indentations and typical of amorphous powders.

Dry Powder Characterizations: LOD), RF/Fill, SEM, and Oxytocin Assay

Loss on drying (LOD) was measured by thermogravimetric analysis (TGA) with a heat and hold method (20° C./min, 110° C. isotherm for 30 minutes). The powders were obtained with an average yield of 73.8% and a minimum LOD of 4.63%.

Aerodynamic performance of the spray-dried powders was measured by Andersen Cascade Impaction with the Gen2C inhaler (30 Lpm, 8 s, MannKind Corp.) and the results are shown in Table 5. Geometric particle size was determined by laser diffraction using a Sympatec RODOS M powder disperser set at 0.5 bar and 3 bar dispersing pressures. Particle morphology was assessed by field emission scanning electron microscopy. Table 5 shows that particles range in size from about 3.8 to 5.6 μm at 0.5 bar and 3 bar atmospheric pressures tested and had a % RF/fill of about 40 to about 60%. As see in Table 5, the samples containing citrate and zinc (Sample ID No. 2, 3 and 4) performed best as shown by the cartridge emptying data (>70%) and emitted dose of 56% to 60%. Density of the powders was evaluated with a tapped density analyzer (Autotap) after 3000 taps. Density of the bulk powder didn't exceed 0.5 g/ml regardless of salt contents.

Oxytocin content was evaluated using an HPLC method. Oxytocin standard solutions were prepared at approximately 250 μg/mL in 0.1M sodium bicarbonate pH 9.5 (6.25 mg of oxytocin raw material in 25.0 mL). Powders were prepared by dissolving 10±1.0 mg in 0.1M sodium bicarbonate pH 9.5 to give a final oxytocin concentration of 0.250 mg/mL. Initial drug content was assayed to ascertain the starting material. Powders were prepared with a target drug content of 1% and assays confirmed the oxytocin content between 0.92 and 1.13%.

Oxytocin Stability in Powder Form

The powders were weighed into 20 mL glass vials that were then closed, wrapped in foil, and heat sealed. The foil pouches were placed on a stability chamber at 40° C./75% RH. Samples were pulled at 2 and 4 weeks; then pulled every 4 weeks and up to 32 weeks after incubation. Samples were stored frozen (−20° C.) until assayed by HPLC as discussed above.

TABLE 4

Stability results for oxytocin powders at 40° C./75% RH

| ID No. | t = 0 | t = 2 W | t = 4 W | t = 8 W | t = 12 W | t = 16 W | t = 20 W | t = 24 W | t = 28 W | t = 32 W | t = 36 W | t = 40 W | t = 44 W |
|---|---|---|---|---|---|---|---|---|---|---|---|---|---|
| 1 | 100 | 87.8 | 68.3 | 67.6 | 69.1 | 69.5 | 59.8 | 61.3 | 57.0 | 51.6 | | | |
| 2 | 100 | 90.3 | 87.1 | 86.4 | 83.2 | 81.9 | 79.9 | 77.8 | 12.7 | 75.7 | | | |
| 3 | 100 | 91.9 | 89.8 | 88.2 | 86.8 | 84.6 | 79.3 | 81.1 | 78.1 | 79.1 | | | |
| 4 | 100 | 94.1 | 95.8 | 94.0 | 94.1 | 89.5 | 90.0 | 87.3 | 90.2 | 89.2 | 82.8 | 82.3 | 81.6 |
| 5 | 100 | 98.1 | 94.0 | 93.5 | 88.8 | 87.0 | 84.9 | 80.5 | 82.5 | 81.6 | | | |
| 6 | 100 | 99.1 | 97.8 | 97.8 | 93.2 | 95.6 | 94.9 | 91.5 | 92.9 | 101.4 | 101.4 | 89.4 | 90.0 |
| 7 | 100 | 91.4 | 90.1 | 88.9 | 86.5 | 78.2 | 73.2 | 70.1 | 73.0 | 67.6 | | | |
| 8 | 100 | 95.9 | 91.1 | 86.4 | 55.3 | 71.7 | 60.7 | 71.7 | 63.4 | 60.3 | | | |
| 9 | 100 | 94.9 | 94.1 | 92.5 | 88.0 | 82.2 | 81.3 | 78.3 | 74.2 | 66.1 | | | |
| 10 | 100 | 89.6 | 85.6 | 67.3 | 59.8 | 51.1 | 50.0 | 49.1 | 46.4 | 46.6 | | | |
| 11 | 100 | 99.3 | 89.5 | 88.2 | 83.5 | 77.5 | 73.8 | 76.2 | 73.6 | 72.4 | | | |
| 12 | 100 | 94.4 | 93.1 | 87.0 | 84.5 | 78.9 | 83.7 | 82.0 | 79.1 | 76.4 | | | |
| 13 | 100 | 98.8 | 94.2 | 93.3 | 91.0 | 91.7 | 89.5 | 90.3 | 92.5 | 92.0 | 93.6 | 87.6 | 83.2 |

TABLE 5

Aerodynamic performance, particle size and density characterizations

| ID No. | Aerodynamic performance (30 LPM, 8 s) | | | Particle size (μm) | | Density (g/l) | |
|---|---|---|---|---|---|---|---|
| | % RF | % RF/fill | % CE | 0.5 bar | 3 bar | $D_{Bulk}$ | $D_{Tap}$ |
| 1 | 58.4 | 40.9 | 70.0 | 4.06 | 3.85 | 0.411 | 0.553 |
| 2 | 76.5 | 59.1 | 77.2 | 4.09 | 3.86 | 0.472 | 0.594 |
| 3 | 77.5 | 60.3 | 77.8 | 4.13 | 3.98 | 0.408 | 0.582 |
| 4 | 71.4 | 55.4 | 77.3 | 4.12 | 4.07 | 0.456 | 0.623 |
| 5 | 74.3 | 55.9 | 75.3 | 4.18 | 3.96 | 0.454 | 0.649 |
| 6 | 69.4 | 59.8 | 86.2 | 4.22 | 4.16 | 0.389 | 0.620 |
| 7 | 72.8 | 42.5 | 58.3 | 5.62 | 5.61 | — | — |
| 8 | — | — | — | 4.10 | 4.02 | — | — |
| 9 | — | — | — | 4.38 | 4.29 | — | — |
| 10 | 68.8 | 59.5 | 86.4 | 4.05 | 3.86 | — | — |
| 11 | 56.4 | 50.6 | 89.6 | 5.25 | 4.90 | — | — |
| 12 | — | — | — | 4.07 | 3.83 | — | — |
| 13 | 70.8 | 53.2 | 75.1 | 4.17 | 4.00 | 0.397 | 0.580 |

Aerodynamic Performance, Particle Size and Morphology

Aerodynamic testing on selected powders highlighted the beneficial effect of combining sodium citrate and zinc with trehalose, isoleucine and PVP. The effect was observed with citrate and zinc contents as low as 4.8% and 1.3% respectively (Table 5, Sample ID No. 4). The maximum effect (60.3% RF/fill) was obtained with 12% citrate content and 3.4% zinc. Powder Sample ID No. 2, prepared with twice the amount of citrate and zinc, had an RF/fill of 59.1%. Both Sample powders ID Nos. 2 and 4 when tested in the inhaler were delivered out of the inhaler at about 77% of the original content. The RF/fill of the control powder (Sample ID No. 1) formulated with trehalose, isoleucine and PVP (87/10/2) was 40.9% and at a rate less than the samples containing zinc and citrate.

Figure 2A:
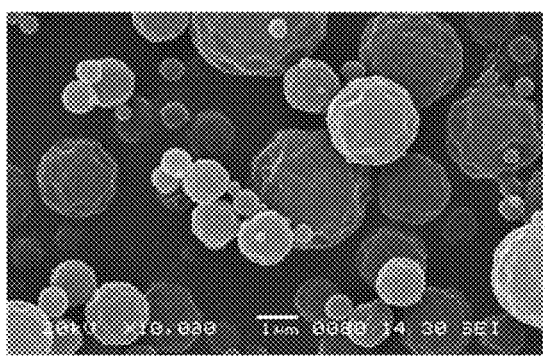
FIG. 2A is a scanning electron micrograph of a control powder similar to FIG. 1B at high magnification.
Figure 2B:
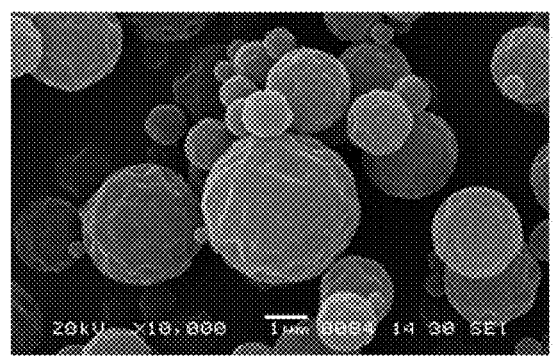
FIGS. 2B, 2C and 2D are scanning electron micrographs of an amorphous dry powder formulation embodiments comprising 1% oxytocin; citrate and a zinc salt at high magnification and containing differing amounts of divalent zinc salts and citrate salts.
Figure 2C:
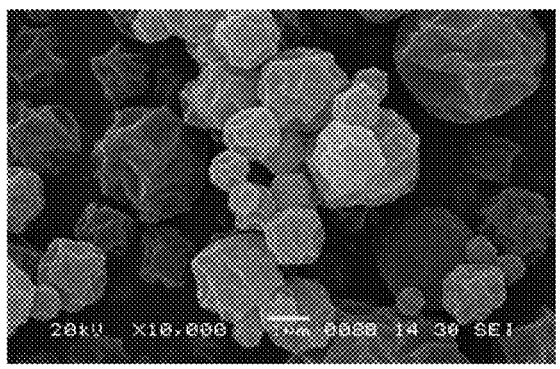
Figure 2D:
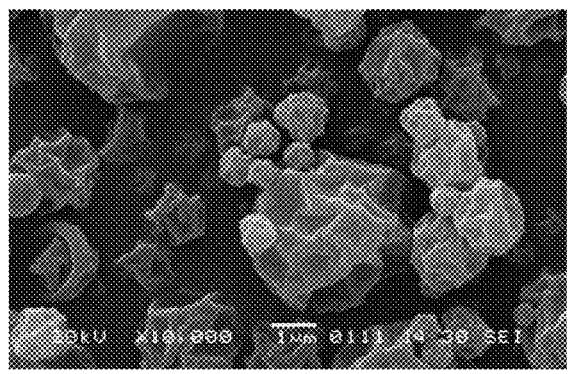

Particle morphology studied by scanning electron microscopy shows that spray-drying of the control formulation (Sample ID No. 1) containing trehalose, PVP and isoleucine produced slightly corrugated, spherical particles typical of leucine-containing powders (FIG. 2A). The corrugated substantially spherical morphology was maintained with the addition of salts (zinc and citrate salts) to the mixture containing trehalose, PVP and isoleucine (FIGS. 2B; 2C and 2D). However, the particles containing zinc and citrate differ from the controls as they appear slightly more corrugated and less spherical. As shown in the SEMs, the particles formed with zinc and/or citrate appear substantially spherical and have a slightly more indentations, corrugated surface or wrinkle appearance, and less regular pattern. It was observed that the particles containing oxytocin, zinc and citrate appeared to be more fragile or more collapsible than the controls during preparation in particular during vacuum drying step.

Figure 4:
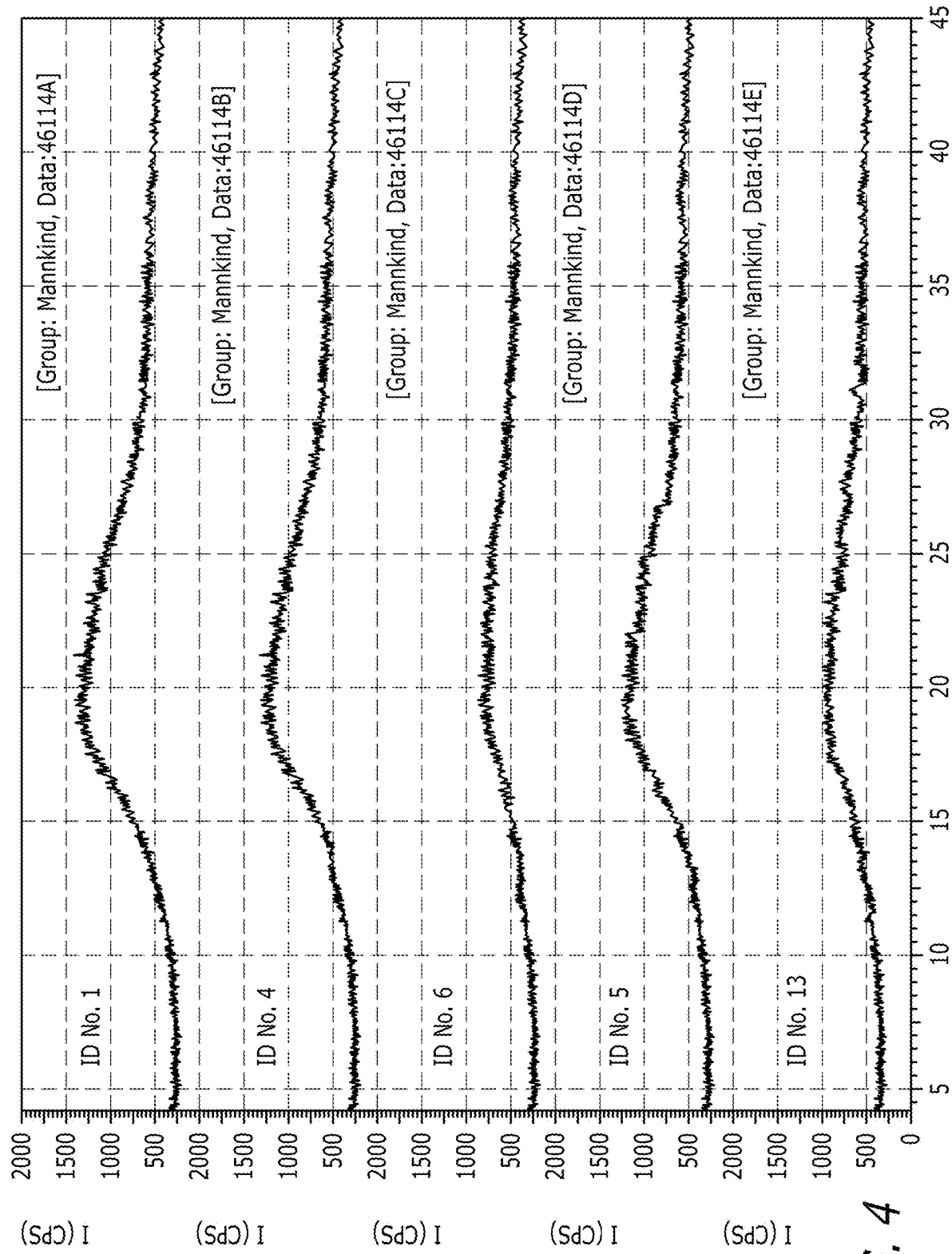
FIG. 4 provides a graphic representation of data obtained from X-ray diffraction studies of dry powders showing amorphous content of the powders by their characteristic scan patterns.

FIG. 4 provides a graphic representation of data obtained from X-ray diffraction studies of dry powders showing amorphous content of the powders by their characteristic scan patterns. The data demonstrates that the X-ray diffraction analysis confirmed that the spray-dried powders all appear as uniform amorphous in content as demonstrated by data scans depicted in FIG. 4.

The data also demonstrates that the addition of citrate/zinc to a powder containing FDKP (Sample ID No. 7) (19.5% w/w), trehalose (38.4% w/w) and isoleucine (6.5% w/w) produced a powder with improved properties (42% RF/fill) over the powder without citrate and zinc. The powder containing citrate yielded a 17% improvement in RF/fill over a powder formulated without citrate/zinc (25.6% RF/fill, 78.4% CE).

The present powders were not excessively cohesive because their median geometric particle sizes were similar at 0.5 bar and 3 bar RODOS dispersing pressures. The average values were 4.34 and 4.18 μm at 0.5 and 3 bars.

The data in Table 5 show the aerodynamic performance of the powders. Table 5 shows that the powders containing citrate and zinc yielded high respirable fractions (>70%) and cartridge emptying data in some instances were greater than >90% (data not shown). Sample testing in an anatomically correct airway model showed that about 73% of the dose in an inhaler containing the powders is delivered to the lungs.

Oxytocin Stability Studies

The data indicate that out of the fourteen powders prepared, three maintained more than 89% of the original total oxytocin content obtained after 32 weeks of incubation at 40° C./75% RH (Table 4). The degradation rate appears to be the highest before 4 weeks for the most stable powders (FIG. 3) then plateaus; this early onset of degradation is probably due to moderate to high residual water content in the powders. The most stable powders was prepared from a pH 6.5 citrate buffer and zinc chloride as a source of zinc divalent cations. Overall, powders prepared in presence of both citrate and zinc salts exhibited the highest stability. The stabilizing effect of this combination was even observed at low salts contents (Sample ID No. 1 vs. Sample ID Nos. 2, 3, 4). Among the "non-buffered" formulations, the addition of disodium FDKP or replacing isoleucine by trileucine or cystine enhanced the stability of the powders.

Example 2

Preparation, Characterization and Stability of Alternative Oxytocin Spray-Dried Powder Embodiments Preparation of oxytocin spray-dried powders was performed as in Example 1 above. In these experiments, fourteen powders containing 1% (w/w) oxytocin and varying amounts of buffers, salts, carries excipients, including, trehalose, PVP, isoleucine, sodium citrate, citric acid, sodium tartrate, tartaric acid and zinc salt, obtained from various vendors as described in Table 6 below, were prepared at the 2.5 g scale as shown on Table 1 below. In these experiments, L-(+)-tartaric acid and sodium L-(+)-tartrate dihydrate were used and obtained from Alfa Aesar. Unlike in Example 1, bulk solid sodium citrate salt and citric acid were used as source of sodium citrate. Samples containing 1% (w/w) oxytocin were made as described in Example 1 and the solutions or suspensions were then spray-dried using the parameters as described in Table 6 below.

The dry powders were collected and used in the experiments described below. Powders identified with sample numbers ID Nos. 14 to 28 were obtained with an average yield of 76.7% and a minimum loss on drying (LOD) of 5.73% (measured by Karl Fisher titration). Powders ID Nos. 14 to 28 were submitted to an additional drying step under vacuum pump that led to a minimum LOD of 2.90%.

Spray-dried powders containing a target oxytocin content of 1% were assayed and the data confirmed the oxytocin values ranged between 0.87 to 1.01%. The components of the prepared formulations are detailed in Table 7 showing the contents of each sample made and tested. In certain embodiments, a mixture having a ratio of 87:10:2 by weight of trehalose, isoleucine and PVP served as a matrix for all the formulations except samples ID No. 20 and 21. To this mixture sodium citrate, citric acid and zinc were added. The quantities of citrate salts were varied from 100 to 50 equivalents per mole of oxytocin (29.2 to 14.6% of total weight). The quantities of the zinc salts were varied from 50 to 5 equivalents per mole of oxytocin (30.3 to 0.7% of total weight). In some embodiments, the zinc cation appeared to be essential to the composition characteristics as exemplified by zinc chloride use alone (Sample ID No. 22) also provided improved stability of the powders.

TABLE 6

Drying Conditions

| | |
|---|---|
| Inlet: | 150° C. |
| Outlet: | 70° C. |
| Drying gas flow: | 60 mbar (nitrogen) |
| Atomization flow: | ~59.9 g/h |
| Aspirator | 80% |
| Pump | 5% |

TABLE 7

Oxytocin Sample compositions

Wt. % Target (dry basis)

| Sample ID No. | Sodium citrate | Citric acid | $ZnCl_2$ | Trehalose | ILE | PVP |
|---|---|---|---|---|---|---|
| 14 | 29.2 | — | 6.8 | 56.3 | 6.5 | 1.3 |
| 15 | 29.2 | — | 2.7 | 59.8 | 6.9 | 1.4 |
| 16 | 29.2 | — | 1.4 | 61.0 | 7.0 | 1.4 |
| 17 | 29.2 | — | 0.7 | 61.6 | 7.1 | 1.4 |
| 18 | 14.6 | — | 6.8 | 69.1 | 7.9 | 1.6 |
| 19 | 24.3 | 3.16 | 6.8 | 57.8 | 6.6 | 1.3 |
| 20 | 29.2 | — | 6.8 | 64.0 | — | — |
| 21 | — | — | 6.8 | 57.6 | 6.4 | — |
| 22 | — | — | 6.8 | 81.94 | 9.42 | 1.88 |

Zinc citrate

| 23 | — | — | 30.3 | 61.2 | 7.0 | 1.4 |
| 24 | — | — | 9.1 | 79.9 | 9.2 | 1.8 |
| 25 | 24.3 | 3.16 | 30.30 | 37.07 | 4.26 | 0.85 |
| 26 | 14.6 | — | 30.30 | 48.42 | 5.57 | 1.11 |

| | Sodium tartrate | Tartaric acid | | | | |
|---|---|---|---|---|---|---|
| 27 | 22.8 | — | 6.8 | 61.9 | 7.1 | 1.4 |
| 28 | 19.0 | 3.0 | 6.8 | 62.6 | 7.2 | 1.4 |

Aerodynamic Performance of Dry Powders

Aerodynamic performance of the spray-dried powders was measured by Andersen Cascade Impaction with the Gen2C inhaler (21.6 Lpm, 4 s, MannKind Corp.) and the results are shown in Table 8. High % Rf/fill (>50%) were obtained even under a low peak inspiratory pressure. The data in Table 8 Shows the % RF/fill ranging from about 20 to about 60% and cartridge emptying of total contents was up to 77% (Sample ID No. 22). The highest % Rf/Fill were obtained for powders containing zinc citrate, zinc chloride with or without PVP. As seen in Table 8, % Rf/fill was improved by the addition of isoleucine (Sample ID Nos. 14 and 20). The samples containing zinc citrate or zinc chloride alone (Sample ID Nos. 22, 23 and 24) had high % Rf/fill of about 50 to 60% and cartridge emptying greater than 70%.

Aerodynamic testing on selected powders highlighted the beneficial effect of combining sodium citrate and zinc chloride with trehalose, isoleucine with or without PVP as exemplified by Sample ID No. 18, 19, 20 and 21. The improved performance of the powders was observed with citrate and zinc contents as low as 14.6% and 1.4% respectively (Sample ID Nos. 16 and 18). The maximum effect (53.0% RF/fill) was obtained with 14.6% content in sodium citrate and 6.8% in zinc (Sample ID No. 18). The beneficial effect of combining zinc citrate with trehalose, isoleucine and PVP is exemplified by the performance of powders Sample ID Nos. 23 and 24, which yielded % Rf/fill greater than 50% and cartridge emptying of about 73%.

TABLE 8

Aerodynamic performance by Andersen cascade impactor.

| Sample ID No. | % RF/fill | % CE |
|---|---|---|
| 14 | 43.3 | 57.2 |
| 15 | 47.3 | 62.1 |
| 16 | 49.8 | 61.2 |
| 17 | 22.4 | 35.3 |
| 18 | 53.0 | 71.9 |
| 19 | 44.8 | 61.6 |
| 20 | 36.0 | 52.4 |
| 21 | 50.3 | 66.9 |
| 22 | 51.2 | 77.0 |
| 23 | 51.5 | 73.0 |
| 24 | 60.3 | 72.7 |
| 25 | 37.5 | 55.0 |
| 26 | 37.7 | 59.3 |
| 27 | 57.3 | 74.7 |
| 28 | 45.1 | 59.6 |

Oxytocin Formulation Stability Studies

Figure 5:
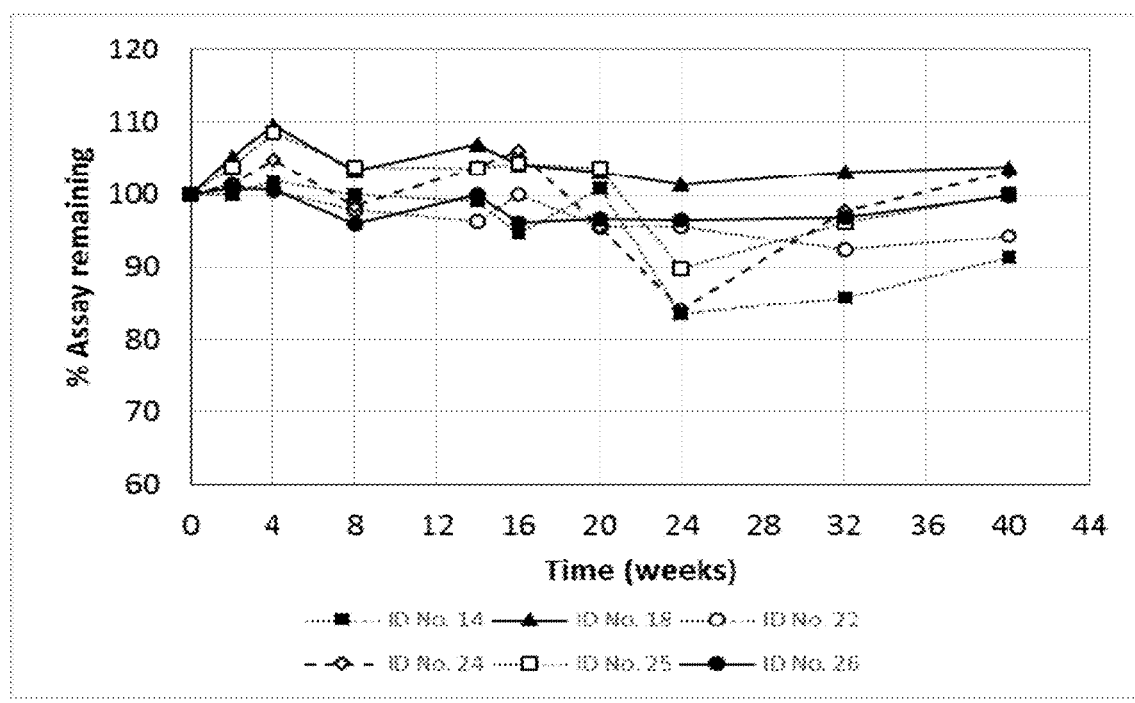
FIG. 5 is a graphic representation of dry powder samples from the stability studies wherein the samples contained divalent zinc salt and citrate salts at various concentrations.

Stability of oxytocin spray-dried powders was performed as in Example 1 above. Stability testing was performed up to 40 weeks. The oxytocin stability study results from the assays are shown in Table 9 below and FIG. 5. The data is shown as the percent (%) remaining of sample compared to the starting material used. As seen in Table 9, only 3 of the powder formulations (Sample ID Nos. 16, 27, and 28) tested maintained less than about 90% of the oxytocin when aliquots of the sample were assayed after 40 weeks incubation. The combination of citrate and zinc salts led to the highest stability in solid state (greater than about 90%). The highest stability was achieved with the combination containing 14.6% sodium citrate and 6.8% zinc chloride (Sample ID No. 18). Powders containing a minimum 9.1% content in zinc citrate with or without sodium citrate maintained more than 97% of the oxytocin after 40 weeks incubation. FIG. 5 is a graphic representation of dry powder samples from the stability studies wherein the samples containing divalent zinc salt and citrate salts at various concentrations showed a slow degradation of the oxytocin over a period of 40 weeks; wherein the samples tested retained greater than 90% of the oxytocin content.

In the alternative embodiment using tartrate, powders containing zinc and tartrate salts maintained also about 90% of the oxytocin content after 24 weeks of incubation and greater than 85% of the oxytocin content after 32 weeks of sample incubation.

TABLE 8

Stability results for oxytocin powders at 40° C./75% RH

| ID No. | t = 0 | t = 2 W | t = 4 W | t = 8 W | t = 14 W | t = 16 W | t = 20 W | t = 24 W | t = 32 W | t = 40 W |
|---|---|---|---|---|---|---|---|---|---|---|
| 14 | 100 | 99.9 | 101.9 | 100.0 | 99.1 | 94.6 | 100.9 | 83.5 | 85.8 | 91.4 |
| 15 | 100 | 98.5 | 104.2 | 97.8 | 97.5 | 96.0 | 93.5 | 78.0 | 74.3 | 95.7 |
| 16 | 100 | 100.2 | 102.2 | 94.9 | 96.0 | 100.8 | 55.1 | 79.7 | 41.7 | 33.9 |
| 17 | 100 | 97.0 | 99.7 | 96.7 | 96.5 | 93.7 | 94.3 | 91.1 | 85.3 | 90.1 |
| 18 | 100 | 105.2 | 109.5 | 103.3 | 107.0 | 104.2 | 103.2 | 101.4 | 103.1 | 103.8 |
| 19 | 100 | 103.5 | 102.2 | 102.4 | 102.1 | 101.5 | 101.6 | 92.8 | 94.6 | 96.9 |
| 20 | 100 | 103.5 | 104.5 | 103.1 | 103.2 | 103.3 | 105.1 | 93.3 | 101.4 | 96.0 |
| 21 | 100 | 100.2 | 100.9 | 101.2 | 101.2 | 101.2 | 99.6 | 99.3 | 93.3 | 92.9 |
| 22 | 100 | 101.4 | 100.5 | 98.0 | 96.3 | 100.1 | 95.7 | 95.6 | 92.4 | 94.2 |
| 23 | 100 | 99.6 | 97.6 | 100.1 | 99.0 | 101.0 | 100.8 | 97.7 | 88.7 | 97.3 |
| 24 | 100 | 101.4 | 104.9 | 98.4 | 103.8 | 106.0 | 95.6 | 84.2 | 97.8 | 103.1 |
| 25 | 100 | 103.8 | 108.4 | 103.8 | 103.6 | 104.4 | 103.7 | 89.7 | 96.2 | 100.0 |
| 26 | 100 | 100.9 | 100.7 | 96.0 | 100.0 | 96.1 | 96.7 | 96.6 | 96.9 | 99.8 |
| 27 | 100 | 97.3 | 100.1 | 98.4 | 97.6 | 98.0 | 97.5 | 91.8 | 88.4 | 66.0 |
| 28 | 100 | 102.6 | 102.6 | 100.0 | 99.8 | 98.7 | 94.3 | 93.4 | 86.8 | 88.7 |

The addition of citrate or tartrate and zinc salts to the formulations of oxytocin appeared beneficial for both the aerodynamic performance and oxytocin stability.

Example 3

A pregnant woman, 35 year old and in her second pregnancy has a history of mild post-partum hemorrhaging in her first pregnancy is admitted to the hospital at 40 weeks of pregnancy and in labor. Contractions are monitor to occur 5 minutes apart by the attending obstetrician. The pregnant woman is noted to be bleeding and delivers a healthy baby. In the operating room and immediately upon childbirth, the woman is administered by oral inhalation a dry powder formulation containing a single dose of 100 IU of oxytocin, 28% (w/w) citrate and 7% (w/w) zinc chloride, in a single inhalation, using an inhalation system comprising a high resistance inhaler as described in U.S. Pat. No. 8,484,129, which disclosure is incorporated herein by reference in its entirety for its teaching of the relevant subject matter. The woman was kept in the hospital for 3 days and did not suffer any severe bleeding and was released with her newborn baby.

Unless otherwise indicated, all numbers expressing quantities of ingredients, properties such as molecular weight, reaction conditions, and so forth used in the specification, and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A dry powder pharmaceutical formulation comprising inhalable microparticles of a diketopiperazine comprising oxytocin, an oxytocin derivative or an oxytocin analog, and zinc citrate or zinc chloride, and/or a pharmaceutically acceptable carrier or excipient, wherein the pharmaceutical formulation is stable for at least 40 weeks at 40° C. and 75% relative humidity.

2. The dry powder pharmaceutical formulation of claim 1, comprising zinc citrate.

3. The dry powder pharmaceutical formulation of claim 1, wherein the pharmaceutically acceptable carrier or excipient is a sugar selected from mannose, mannitol, trehalose, or sorbitol.

4. The dry powder pharmaceutical formulation of claim 1, wherein the pharmaceutically acceptable carrier or excipient is polyvinylpyrrolidone or polyethylene glycol.

5. The dry powder pharmaceutical formulation of claim 1, wherein the diketopiperazine is fumaryl diketopiperazine or succinyl diketopiperazine.

6. The dry powder pharmaceutical formulation of claim 1, wherein the zinc citrate is in an amount ranging from 100 to 20 equivalents per mole of the oxytocin, the oxytocin analog or derivative thereof.

7. A pharmaceutical dry powder formulation for inhalation comprising inhalable microparticles of a diketopiperazine comprising oxytocin, an analog of oxytocin or a derivative of oxytocin; zinc chloride in an amount ranging from about 1% to about 7% (w/w) of the formulation, and a pharmaceutically acceptable excipient, wherein the pharmaceutical formulation is stable for at least 40 weeks at 40° C. and 75% relative humidity.

8. The dry powder pharmaceutical formulation of claim 5, wherein the diketopiperazine is fumaryl diketopiperazine.

9. The dry powder formulation of claim 1, wherein said microparticles of a diketopiperazine comprise microparticles having a diameter of between about 0.5 to about 10 microns.

10. The dry powder pharmaceutical formulation of claim 7, wherein the diketopiperazine is fumaryl diketopiperazine.

11. The dry powder formulation of claim 7, wherein said microparticles of a diketopiperazine comprise microparticles having a diameter of between about 0.5 to about 10 microns.

* * * * *